US011266704B2

(12) United States Patent
Chen et al.

(10) Patent No.: US 11,266,704 B2
(45) Date of Patent: Mar. 8, 2022

(54) **TOTAL FLAVONOID EXTRACT FROM *GYNURA FORMOSANA* KITAM., PREPARATION METHOD THEREOF, AND USE OF SAME IN TREATING NON-ALCOHOLIC FATTY LIVER DISEASE**

(71) Applicant: ZHANGZHOU PIEN TZE HUANG PHARMACEUTICAL CO., LTD., Fujian (CN)

(72) Inventors: Zhiliang Chen, Fujian (CN); Jinming Huang, Fujian (CN); Juan Yu, Fujian (CN); Fei Hong, Fujian (CN); Zhaoqiang Zhang, Fujian (CN); Xuxin Li, Fujian (CN)

(73) Assignee: ZHANGZHOU PIEN TZE HUANG PHARMACEUTICAL CO., LTD., Fujian (CN)

(*) Notice: Subject to any disclaimer, the term of this patent is extended or adjusted under 35 U.S.C. 154(b) by 0 days.

(21) Appl. No.: 16/821,334

(22) Filed: Mar. 17, 2020

(65) Prior Publication Data

US 2020/0215141 A1 Jul. 9, 2020

Related U.S. Application Data

(63) Continuation of application No. PCT/CN2018/101167, filed on Aug. 17, 2018.

(30) Foreign Application Priority Data

Sep. 18, 2017 (CN) .......................... 201710840946.2

(51) Int. Cl.
| | |
|---|---|
| *A61K 36/00* | (2006.01) |
| *A61K 36/287* | (2006.01) |
| *A61P 1/16* | (2006.01) |
| *A61K 9/00* | (2006.01) |
| *A61K 9/02* | (2006.01) |
| *A61K 9/06* | (2006.01) |
| *A61K 9/12* | (2006.01) |
| *A61K 9/16* | (2006.01) |
| *A61K 9/20* | (2006.01) |
| *A61K 9/48* | (2006.01) |

(52) U.S. Cl.
CPC .......... *A61K 36/287* (2013.01); *A61K 9/0019* (2013.01); *A61K 9/0095* (2013.01); *A61K 9/02* (2013.01); *A61K 9/06* (2013.01); *A61K 9/12* (2013.01); *A61K 9/16* (2013.01); *A61K 9/20* (2013.01); *A61K 9/4808* (2013.01); *A61P 1/16* (2018.01); *A61K 2236/331* (2013.01); *A61K 2236/39* (2013.01)

(58) Field of Classification Search
CPC ........................................................ A61K 36/00
USPC ...................................................... 424/725
See application file for complete search history.

(56) References Cited

U.S. PATENT DOCUMENTS

| | | |
|---|---|---|
| 2001/0014669 A1 | 8/2001 | Bok et al. |
| 2020/0215140 A1 | 7/2020 | Chen et al. |
| 2020/0222484 A1 | 7/2020 | Yuan et al. |

FOREIGN PATENT DOCUMENTS

| | | |
|---|---|---|
| CN | 101336949 A | 1/2009 |
| CN | 101953866 A | 1/2011 |
| CN | 104151380 A | 11/2014 |
| CN | 104173458 A | 12/2014 |
| CN | 107582587 A | 1/2018 |
| CN | 107582588 A | 1/2018 |
| CN | 107582589 A | 1/2018 |
| CN | 107582590 A | 1/2018 |
| CN | 107625800 A | 1/2018 |
| JP | 2002524522 A | 8/2002 |
| JP | 2020534357 A | 11/2020 |
| JP | 2020537538 A | 12/2020 |

OTHER PUBLICATIONS

International Search Report, International Application No. PCT/CN2018/101168.
Written Opinion dated Nov. 2018, Application No. PCT/CN2018/101168.
English Translation of the First Office Action, Application No. 2017108416339.
Yao, L., et al., "Research Process of Chemical Constituents and Biological Activities of the Genus *Gynura* Plants," Journal of Northern Horticulture, No. 24, (2016) (English translation).
Luo, Y., "Introduction to Food Biotechnology," China Agricultural University Press, pp. 325-326 (Aug. 31, 2016).
Lin, Y., et al.,, "Optimization the Extraction of Total Flavonoids from Gynura Formosana Kitam Guided by Ultrasounds and Research on its Antibacterial Activity In Vitro," Journal of Youjiang Medical University for Nationalities, vol. 39, No. 2, pp. 90-93, Apr. 2017.
Zhang, R., "Practical Ophthalmic Pharmacology," People's Military Medical Press, p. 388, Sep. 30, 2015.
Wang, C., et al., "Treatment of Chronic Illness," Clinical Practice of Functional Medicine, pp. 232, May 2017.
Wan, et al., "Therapeutical Effect of Gynura Formosana Alcohol Extract on Nonalcoholic Fatty Liver Disease in Rats," Global Journal of Integrated Chines Medicine and Western Medicine, vol. 2, No. 2, pp. 1-6, Jul. 2014.
Yao Liangliang, et al., "Research Process of Chemical Constituents and Biological Activities of the Genus *Gynura* Plants," Journal of Northern Horticulture, No. 24, p. 195-200, Dec. 30, 2016.

(Continued)

*Primary Examiner* — Michael V Meller
(74) *Attorney, Agent, or Firm* — Elmore Patent Law Group, P.C.; Joseph Zucchero; Carolyn Elmore

(57) ABSTRACT

A total flavonoid extract from *Gynura formosana* Kitam., comprising 80-85% of rutin. A preparation method comprises selecting a complex enzyme consisting of a specific composition and ratio of enzymes for enzymatic hydrolysis, extracting and concentrating by a macroporous resin, and separating and purifying by a macroporous resin. The extract has therapeutic effect on non-alcoholic fatty liver disease.

13 Claims, 3 Drawing Sheets

(56) References Cited

OTHER PUBLICATIONS

Pan, Ran et al, "Rutin Inhibits Oleic Acid Induced Lipogenesis in Hepatocyte Cells via Regulating TG Metabolic Pathway," Journal of Yunnan University of Traditional Chinese Medicine, vol. 38 No. 5, pp. 1-6, published on Oct. 30, 2015.
English translation of the Second Office Action, dated Sep. 17, 2020, in priority Chinese Application No. 201710840946.2.
First Office Action in corresponding Japanese Application No. 2020-537272 dated Aug. 3, 2017.
Liu, Q., et al., "Rutin Exhibits Hepatoprotective Effects in a Mouse Model of Non-Alcoholic Fatty Liver Disease by Reducing Hepatic Lipid Levels and Mitigating Lipid-Induced Oxidative Injuries," International Immunopharmacology, vol. 49, pp. 132-141, 2017.
Panchal, S., et al., "Rutin Attenuates Metabolic Changes, Nonalcoholic Steatohepatitis, and Cardiovascular Remodeling in High-Carbohydrate, High-Fat Diet-Fed Rats," The Journal of Nutrition, pp. 1062-1069.
Decision of Refusal of Corresponding Chinese Application No. 201710840946.2, dated Dec. 28, 2020.
First Office Action in corresponding Korean Application No. 9-5-2021-064233616, dated Oct. 26, 2021.
Hou, W.C., et al., "The Phenolic Consitituents and Free Radical Scavenging Activities of Gynura formosana Kiamnra," Journal of the Science of Food and Agriculture, 85: pp. 615-621 (2005).
Yun, W., et al., "Therapeutical Effect of Gynura formosana Alcohol Extract on Nonalcoholic Fatty Liver Disease in Rats," GJICMWM, vol. 2, No. 2, 2014.
Wong, L., et al., "Effect of Total Flavonoids in Gynura divaricata (L.) DC. on Blood Lipid and Liver of Rats with Hyperlipidemia," Capital Journal of Public Health, vol. 10, No. 5, Oct. 2016.
Zhang, X., Selected Questions and Answers of Shanghai Sannong Service Hotline, Shanghai Scientific & Technical Publishers, p. 72.
English Translation of the First Office Action in corresponding Japanese Application No. 2020-537272 dated Jul. 29, 2021.
English Translation of Decision of Refusal of Corresponding Chinese Application No. 201710840946.2, dated Dec. 28, 2020.
English Translation of the Notification of Reasons for Refusal of corresponding Korean Application No. 10-2020-7011230, dated Oct. 26, 2021.
Yun, W., et al., "Therapeutical Effect of Gynure formosana Alcohol Extract on Nonalcoholic Fatty Liver Disease in Rats," GJICMWM, vol. 2, No. 2, 2014.

TOTAL FLAVONOID EXTRACT FROM *GYNURA FORMOSANA* KITAM., PREPARATION METHOD THEREOF, AND USE OF SAME IN TREATING NON-ALCOHOLIC FATTY LIVER DISEASE

CROSS-REFERENCE TO RELATED APPLICATIONS

This application is a continuation application of International Patent Application No. PCT/CN2018/101167 with an international filing date of Aug. 17, 2018, designating the United States, and further claims priority benefits to Chinese Patent Application No. 201710840946.2, filed on Sep. 18, 2017. The contents of all of the aforementioned applications are incorporated herein by reference.

TECHNICAL FIELD

The present invention belongs to the field of medicines or health products, and particularly relates to a total flavonoid extract from *Gynura formosana* Kitam., and preparation method thereof, and use of same for treating non-alcoholic fatty liver disease.

BACKGROUND OF THE INVENTION

Non-alcoholic fatty liver disease (NAFLD) is a clinicopathologic syndrome which does not involve excess alcohol consumption. NAFLD is caused by many factors and shows hepatic stestosis and lipid accumulation. NAFLD includes simple fatty liver and fatty hepatitis, wherein the later may progress into hepatic fibrosis and liver cirrhosis. At present, the prevalence rate of non-alcoholic fatty liver disease is up to 20-30% in the global general population, and more than half of people worldwide will have the risk of developing non-alcoholic fatty liver disease. NAFLD has become the most common liver disease, the incidence of which is obviously higher than the incidence of hepatitis B, hepatitis C and alcoholic liver disease. Epidemiological investigation shows that NAFLD has become one of the common chronic liver diseases in China. The adult prevalence rate of NAFLD reaches 10-25% in developed regions such as Shanghai, Guangzhou and Hong Kong, and the age of people suffering from NAFLD tends to be lower. Fatty liver can progress into irreversible liver injury in a short term, and the incidence rate of fibrosis is up to 25%, and about 10% of patients can develop liver cirrhosis, severely threatening the health of people. Currently, there are no clinically specific drugs for the treatment of NAFLD. Therefore, developing drugs for treating non-alcoholic fatty liver disease has become a hotspot for research. *Gynura formosana* Kitam. also called Bai Bei Tian Kui and Pien Tze Huang grass, is a herbaceous perennial plant of the genus *Gynura* Cass. nom. Cons. in the composite family. *Gynura formosana* Kitam. contains rich vitamins, alkaloids and flavonoid substances, and can be used for both medicine and food. Studies show that *Gynura formosana* Kitam. is mainly used for the treatment of diseases such as pneumonia, lung cancer, hepatitis, liver cirrhosis, hypertension and the like, and also has the effects of clearing away heat and toxic materials. In the prior art, it has been reported that alcohol extracts from *Gynura formosana* Kitam. have a therapeutic effect on rats with non-alcoholic fatty liver disease.

Currently, however, there are no related reports of the treatment of non-alcoholic fatty liver disease with aqueous extract from *Gynura formosana* Kitam. in the prior art.

SUMMARY OF THE INVENTION

The goal of the present invention is to provide a total flavonoid extract from *Gynura formosana* Kitam., and further provide a preparation method thereof and use of same.

The goal of the present invention is realized by the following technical solutions:

In a first aspect, the present invention provides a total flavonoid extract from *Gynura formosana* Kitam., comprising, in weight percent, 80-85% of rutin.

In a second aspect, the present invention also provides a preparation method of the total flavonoid extract from *Gynura formosana* Kitam., comprising the steps of:

(1) Extraction: extracting *Gynura formosana* Kitam., with an extraction solvent to obtain an extraction solution, and adjusting the extraction solution to a pH of 4-8 to obtain a reaction solution;

(2) Enzymolysis: adding a complex enzyme into the reaction solution to carry out enzymolysis through a forced circular reaction at a temperature of 30° C. to 50° C. for 1 to 4 hours, then carrying out suction filtration, and collecting a filtrate;

(3) Extraction and concentration: extracting the filtrate by using a macroporous resin A to obtain an extracted solution, and concentrating the extracted solution to obtain a concentrated solution;

(4) Separation and purification: centrifuging the concentrated solution, collecting a supernatant and carrying out elution by using a macroporous resin B, measuring absorbance at a wavelength of 510 nm, collecting eluate, concentrating and drying the eluate to obtain an extract.

Preferably, in the above preparation method, the complex enzyme used in the enzymolysis step consists of papain, cellulase and pectinase.

Preferably, in the above preparation method, a weight ratio of the complex enzyme to the *Gynura formosana* Kitam. is 1:5 to 1:3.

Preferably, in the above preparation method, a weight ratio of papain to cellulase to pectinase in the complex enzyme is (0.5-1.5):(2-5):(1-3).

Preferably, in the above preparation method, the weight ratio of papain to cellulase to pectinase in the complex enzyme is 1:3:2.

Preferably, in the above preparation method, the macroporous resin A is one or more selected from the group consisting of AB-8, DM-130, HZ841, ZH-00, ZH-01, ZH-02, ZH-03, CAD-40, CAD-45 and BS-30; and the macroporous resin B is one or more selected from the group consisting of D-101, D-140, D-141, XAD-3, XAD-4, HP-20, HP-21, LD-605 and LSA-10.

Preferably, in the above preparation method, the extraction solvent in the extraction step is water, and a weight ratio of *Gynura formosana* Kitam. to water is 1:(20-60).

Preferably, in the above preparation method, in the separation and purification step, an ethanol aqueous solution with a volume concentration of 70-80% is adopted as an elution solvent, and the elution is performed at a rate of 3-15 m/h.

Preferably, in the above preparation method, in the separation and purification step, an ethanol aqueous solution with a volume concentration of 75% is adopted as an elution solvent, and the elution is performed at a rate of 5 m/h.

Preferably, in the above preparation method, the concentrated solution comprises total flavonoid from *Gynura formosana* Kitam. at a concentration of 0.5 mg/mL.

Preferably, in the above preparation method, the extraction and concentration step comprises: placing the filtrate into an extraction tank containing a macroporous resin A, stirring at 30° C. for 6 to 24 hours at 80-150 rpm, then filtering to obtain an absorbed macroporous resin A, adding ethanol solution having a volume concentration of 70-95% to the absorbed macroporous resin A, wherein the ethanol solution is added in an amount 10 to 30 times the weight of the absorbed macroporous resin A, followed by stirring at 30° C. for 6 to 24 hours at 80-150 rpm, and filtering to obtain an extracted solution.

Preferably, in the above preparation method, said adjusting the extraction solution to a pH of 4-8 is carried out with a hydrochloric acid or sodium hydroxide.

Preferably, in the above preparation method, said drying refers to freeze drying.

In a further aspect, the present invention provides a total flavonoid extract from *Gynura formosana* Kitam. prepared by the above preparation method.

In a further aspect, the present invention provides a pharmaceutical preparation, comprising the above mentioned total flavonoid extract from *Gynura formosana* Kitam. or a total flavonoid extract from *Gynura formosana* Kitam. prepared by the above preparation method as an active ingredient, wherein the active ingredient is mixed with a conventional auxiliary material and prepared according to a conventional process into clinically acceptable forms selected from the group consisting of tablets, capsules, powders, mixtures, pills, granules, syrups, plasters, suppositories, aerosols, ointments and injections.

The conventional auxiliary material can be selected from the group consisting of fillers, disintegrants, lubricants, suspending agents, adhesives, sweeteners, flavoring agents, preservatives, matrix and the like. Fillers include starch, pre-gelatinized starch, lactose, mannitol, chitin, microcrystalline cellulose, sucrose, and the like. Disintegrants include starch, pre-gelatinized starch, microcrystalline cellulose, sodium carboxymethyl starch, cross-linked polyvinylpyrrolidone, low substituted hydroxypropyl cellulose, croscarmellose sodium, and the like. Lubricants include magnesium stearate, sodium dodecyl sulfate, talcum powder, silicon dioxide and the like. Suspending agents include polyvinylpyrrolidone, microcrystalline cellulose, sucrose, agar, hydroxypropyl methyl cellulose and the like. Adhesives include starch slurry, polyvinylpyrrolidone, hydroxypropyl methyl cellulose and the like. Sweeteners include sodium saccharin, aspartame, sucrose, sodium cyclamate, glycyrrhetinic acid and the like. Flavoring agents include a sweetener and various essences. Preservatives include paraben, benzoic acid, sodium benzoate, sorbic acid and salts thereof, benzalkonium bromide, chloroethyl acetate, eucalyptus oil and the like. The matrix comprises PEG 6000, PEG 4000, insect wax and the like.

In a further aspect, the present invention provides use of the above mentioned total flavonoid extract from *Gynura formosana* Kitam. or a total flavonoid extract from *Gynura formosana* Kitam. prepared by the above preparation method or the above mentioned pharmaceutical preparation in preparing drug or health product for treating non-alcoholic fatty liver disease.

The technical solutions of the present invention have the following advantages:

(1) According to the present invention, a total flavonoid extract comprising 80-85% of rutin is extracted and separated from *Gynura formosana* Kitam. The efficacy experiment result shows that the extract has a good treatment effect on non-alcoholic fatty liver disease, and can significantly improve the blood lipid metabolic disorder and fatty degeneration in rats with non-alcoholic fatty liver disease, so that the extract can be used as a potential medicine for treating non-alcoholic fatty liver disease.

(2) In the present preparation method of the total flavonoid extract from *Gynura formosana* Kitam., a unique complex enzyme which comprises specific enzymes at specific ratio is adopted for carrying out enzymolysis at 30° C. to 50° C. after the extraction step, so that the structure of the total flavonoid extract is prevented from being damaged at high temperatures, and the total flavonoid compounds can be extracted out to the maximum extent. Further, extraction and concentration with a macroporous resin A and separation and purification with a macroporous resin B are carried out, so that the extraction rate of the total flavonoid compounds of the *Gynura formosana* Kitam. can reach 1.8-2.0%, which is 30% or more higher compared with the extraction rate of the total flavonoid compounds by the existing method. The HPLC purity of rutin in the prepared total flavonoid extract can reach 80-85%.

BRIEF DESCRIPTION OF THE DRAWINGS

The present invention is described in detail with reference to examples and accompanying drawings, wherein.

DETAILED DESCRIPTION OF THE EMBODIMENTS

*Gynura formosana* Kitam. used in the following examples and experimental example of the present invention are taken from Dengke village, Longwen disctrict, Zhangzhou city, Fujian Province, and are identified as the *Gynura formosana* Kitam.

Example 1

Figure 1:
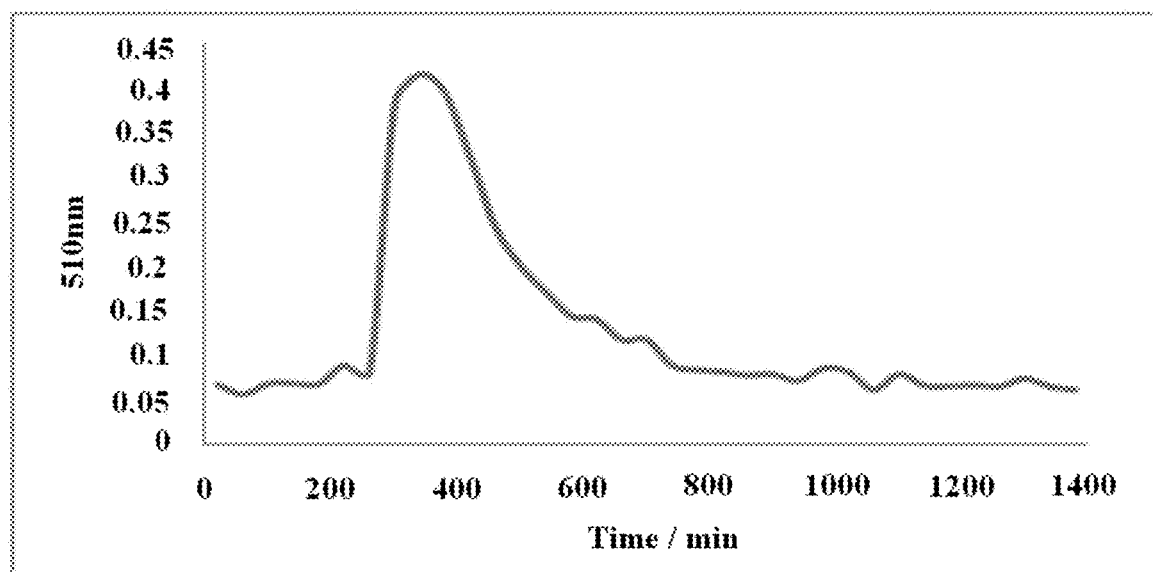
FIG. 1 shows an elution curve in Example 1 of the present invention.

A total flavonoid extract from *Gynura formosana* Kitam. is prepared according to the following method:

(1) Extraction: 100 g *Gynura formosana* Kitam. was added into water with a weight 30 times the weight of *Gynura formosana* Kitam. to carry out extraction, producing an extraction solution, which was then adjusted to a pH of 5, obtaining a reaction solution;

(2) Enzymolysis: 25 g of complex enzyme consisting of papain, cellulase and pectinase with a weight ratio of 1:3:2 was added into the reaction solution to carry out enzymolysis through a forced circular reaction at 40° C. for 3 hours, and the resulted solution was suction filtered and a filtrate was collected;

(3) Extraction and Concentration: The filtrate was added to an extraction tank containing AB-8 macroporous resin and stirred for 12 hours at 30° C. and 100 rpm, then filtered to obtain an absorbed AB-8 macroporous resin. An ethanol solution with a volume concentration of 75% was added to the absorbed AB-8 macroporous resin at an amount 20 times the weight of the absorbed AB-8 macroporous resin, then stirred for 12 hours at 30° C. and 120 rpm and then filtered to obtain an extracted solution. The extracted solution was vacuum concentrated to produce a concentrated solution which comprises a total flavonoid extract from *Gynura formosana* Kitam. at a concentration of 0.5 mg/mL;

(4) Separation and Purification: The concentrated solution was centrifuged at 10,000 rpm for 10 minutes, and a supernatant was collected and placed into a chromatographic column filled with a macroporous resin D-101 for stationary adsorption for 60 min. Then the column was eluted with an aqueous solution of ethanol with a volume concentration of 75% at a rate of 5 m/h, and absorbance was measured at a wavelength of 510 nm. An elution curve was plotted with absorbance as Y-axis versus elution time as X-axis, as shown in FIG. 1. Eluate corresponding to the absorption peak area of the elution curve was collected, concentrated, and freeze-dried to obtain the total flavonoid extract from *Gynura formosana* Kitam.

Through calculation, the extraction rate of the total flavonoid extract from *Gynura formosana* Kitam. is 2.0%.

By referring to FIG. 1, the elution curve of the eluate shows a significant single absorption peak at 340 min, indicating the relatively pure flavonoid in the eluate.

A. The total flavonoid extract from *Gynura formosana* Kitam. was identified with an infrared spectrum according to the following method:

The method comprises the following steps: A certain amount of dried rutin standard was mixed with dried potassium bromide at a weight ratio of 1:100, ground and prepared into a solid pellet. The pellet was then tested with a Fourier infrared spectrophotometer within a scanning range of 4000 $cm^{-1}$ to 400 $cm^{-1}$, a resolution of 4 and a scanning number of 4, thereby obtaining an infrared spectrum. The total flavonoid extract from *Gynura formosana* Kitam. was tested in the same manner to obtain an infrared spectrum. The results are shown in FIG. 2.

Figure 2:
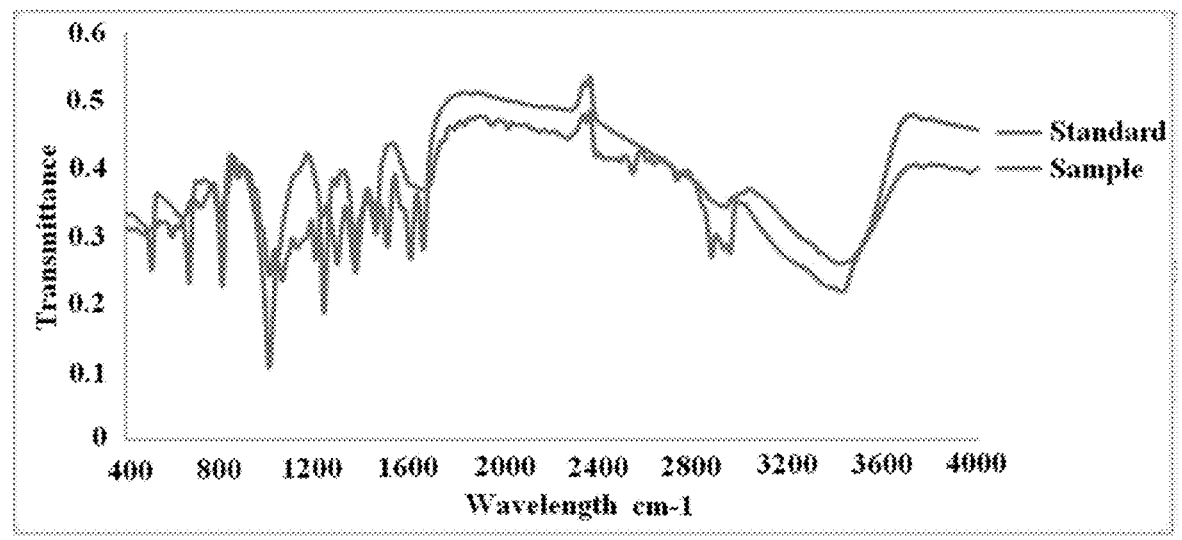
FIG. 2 shows an infrared spectrum of a total flavonoid extract from *Gynura formosana* Kitam. prepared in Example 1 of the present invention.

By referring to FIG. 2, both the infrared spectrums of the rutin standard and the total flavonoid extract from *Gynura formosana* Kitam. show a wide and strong absorption peak around 3685.455 $cm^{-1}$ to 3018.177 $cm^{-1}$, corresponding to telescopic vibration peak of-OH, indicating there are large amount of phenolic hydroxyl groups or sugar hydroxyl groups. A weak absorption peak occurs at 2914.036 $cm^{-1}$, corresponding to a telescopic vibration peak of a carbon-hydrogen bond, indicating less hydrogen on saturated carbon. A strong peak appears at 1654.694 $cm^{-1}$ in each spectrum, corresponding to a telescopic vibration of C=O. The peaks in the two spectrums appear at substantially same position and have substantially same shape, indicating that the extract is a flavonoid. Bending vibration peak of hydroxyl groups appears at 1371.88 $cm^{-1}$ and 1362.89 $cm^{-1}$. An absorption peak caused by ortho hydrogens of phenyl ring appears at 804.80 $cm^{-1}$ and 810.56 $cm^{-1}$. An absorption peak caused by the position of a substituent on the phenyl ring appears at 1010.07 $cm^{-1}$ to 696.62 $cm^{-1}$, but the peak position is different in the two spectrum, indicating the hydroxyl substitution position of the extract is different from that of the rutin standard. These results indicate that the extract contains hydroxyl, carbonyl, and other functional groups such as different position-substituted benzene rings, and the characteristic absorption peaks are substantially consistent. Thus, it can be determined that the extract is a flavonoid compound.

B. The total flavonoid extract from *Gynura formosana* Kitam. was analyzed by liquid chromatography to determine the content of rutin therein according to the following method:

B1. Liquid Chromatography Conditions

Liquid Chromatography Conditions are as follows:

Eclipse XDB-C18 AnalyticalGuard Column (4.6×12.5 mm, 5 μm) and ZOR BZX Eclipse XDB-C18 Column (4.6×150 mm, 5 μm) were used as a protection column. Flow rate is 0.5 mL/min; Column temperature is 35° C. Detection wavelength is 368 nm, 254 nm and 210 nm, respectively; Sample loading volume is 10 μL; Mobile phases consists of (A) 0.03% formic acid aqueous solution and (B) Acetonitrile; Gradient elution procedures are as follows: 0-10 min, 80% (A) and 20% (B); 10-12 min, 76% to 80% (A) and 20% to 24% (B); 12-20 min, 76% (A) and 24% (B); 20-25 min, 70% to 76% (A) and 24% to 30% (B); 25-48 min, 70% (A) and 30% (B).

B2. Preparation of Control Sample Solution 0.001 g Rutin was weighed accurately and dissolved in 1 mL of methanol to prepare a single control sample solution of 1 mg/mL. The control sample solution was filtered with a disposable filter and then loaded into a small test tube for later use.

B3. Determination

The control sample solution and a test sample solution (1 μg/μL methanol solution of the total flavonoid extract prepared in Example 1) are respectively accurately sucked and injected to the liquid chromatography column to perform analysis according to the above mentioned liquid chromatography conditions.

Figure 3:
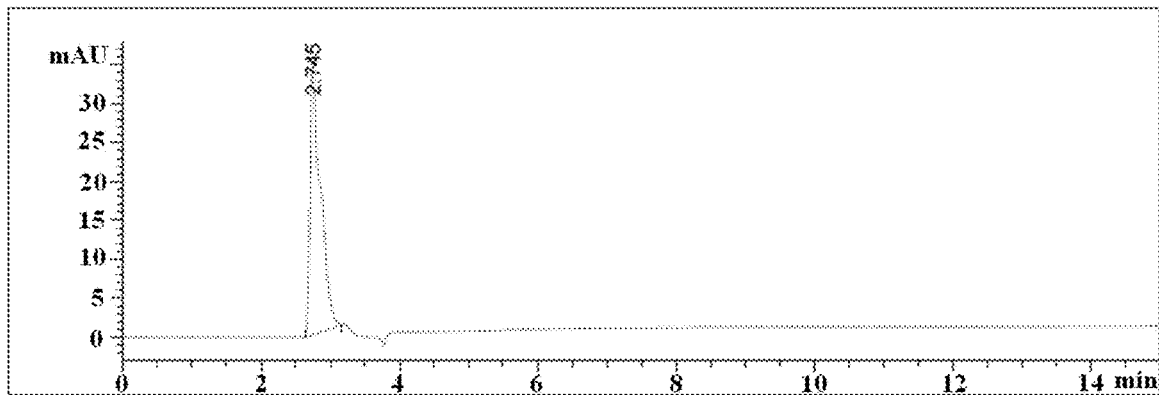
FIG. 3 shows a HPLC chromatogram of a rutin control solution in Example 1 of the present invention.
Figure 4:
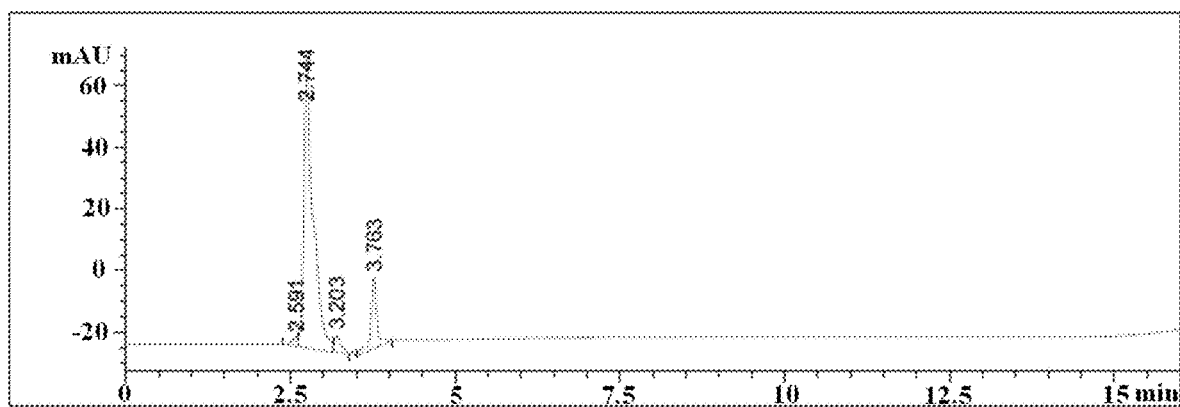
FIG. 4 shows a HPLC chromatogram of the total flavonoid extract from *Gynura formosana* Kitam. prepared in Example 1 of the present invention.

The HPLC chromatogram of the control sample solution is shown in FIG. 3, and the HPLC chromatogram of the test sample solution is shown in FIG. 4.

By referring to FIG. 3, the rutin control solution can be completely isolated within 10 minutes. A substantially straight baseline is observed in the chromatogram of Rutin under the chromatographic conditions of this experiment, and peak tailing is not observed. There are no interfering peaks of impurities. The peaks appear earlier and the retention time is 2.745 min.

By referring to FIG. 4, the amount of rutin in the extract was 81.29% as calculated by area normalization.

Example 2

A total flavonoid extract from *Gynura formosana* Kitam. is prepared according to the following method:

(1) Extraction: 100 g *Gynura formosana* Kitam. was added into water with a weight 20 times the weight of *Gynura formosana* Kitam. to carry out extraction, producing an extraction solution, which was then adjusted with diluted sodium hydroxide solution to a pH of 8, obtaining a reaction solution;

(2) Enzymolysis: 20 g of complex enzyme consisting of papain, cellulase and pectinase with a weight ratio of 0.5:5:1 was added into the reaction solution to carry out enzymolysis through a forced circular reaction at 30° C. for 4 hours, and the resulted solution was suction filtered and a filtrate was collected;

(3) Extraction and Concentration: The filtrate was added to an extraction tank containing DM-130 macroporous resin and stirred for 24 hours at 30° C. and 80 rpm, then filtered to obtain an absorbed DM-130 macroporous resin. An ethanol solution with a volume concentration of 95% was added to the absorbed DM-130 macroporous resin at an amount 10 times the weight of the absorbed DM-130 macroporous resin, then stirred for 24 hours at 30° C. and 80 rpm and then filtered to obtain an extracted solution. The extracted solution was vacuum concentrated to produce a concentrated solution which comprises a total flavonoid extract from *Gynura formosana* Kitam. at a concentration of 0.5 mg/mL;

(4) Separation and Purification: The concentrated solution was centrifuged at 6,000 rpm for 8 minutes, and a supernatant was collected and placed into a chromatographic column filled with a macroporous resin HP-21 for stationary adsorption for 60 min. Then the column was eluted with an aqueous solution of ethanol with a volume concentration of 80% at a rate of 3 m/h, and absorbance was measured at a wavelength of 510 nm. An elution curve was plotted with absorbance as Y-axis versus elution time as X-axis. Eluate corresponding to the absorption peak area of the elution curve was collected, concentrated, and freeze-dried to obtain the total flavonoid extract from *Gynura formosana* Kitam.

Through calculation, the extraction rate of the total flavonoid extract from *Gynura formosana* Kitam. is 1.82%.

The total flavonoid extract from *Gynura formosana* Kitam. was analyzed by liquid chromatography to determine the content of rutin therein according to the method as described in section B of example 1. According to the resulted HPLC chromatogram, the amount of rutin in the total flavonoid extract was 80% in this example.

Example 3

A total flavonoid extract from *Gynura formosana* Kitam. is prepared according to the following method:

(1) Extraction: 100 g *Gynura formosana* Kitam. was added into water with a weight 60 times the weight of *Gynura formosana* Kitam. to carry out extraction, producing an extraction solution, which was then adjusted with a diluted hydrochloric acid to a pH of 4, obtaining a reaction solution;

(2) Enzymolysis: 32 g of complex enzyme consisting of papain, cellulase and pectinase with a weight ratio of 1.5:2:3 was added into the reaction solution to carry out enzymolysis through a forced circular reaction at 50° C. for 1 hour, and the resulted solution was suction filtered and a filtrate was collected;

(3) Extraction and Concentration: The filtrate was added to an extraction tank containing ZH-01 macroporous resin and stirred for 6 hours at 30° C. and 150 rpm, then filtered to obtain an absorbed ZH-01 macroporous resin. An ethanol solution with a volume concentration of 70% was added to the absorbed ZH-01 macroporous resin at an amount 30 times the weight of the absorbed ZH-01 macroporous resin, then stirred for 6 hours at 30° C. and 150 rpm and then filtered to obtain an extracted solution. The extracted solution was vacuum concentrated to produce a concentrated solution which comprises a total flavonoid extract from *Gynura formosana* Kitam. at a concentration of 0.5 mg/mL;

(4) Separation and Purification: The concentrated solution was centrifuged at 8,000 rpm for 5 minutes, and a supernatant was collected and placed into a chromatographic column filled with a macroporous resin XAD-3 for stationary adsorption for 60 min. Then the column was eluted with an aqueous solution of ethanol with a volume concentration of 70% at a rate of 15 m/h, and absorbance was measured at a wavelength of 510 nm. An elution curve was plotted with absorbance as Y-axis versus elution time as X-axis. Eluate corresponding to the absorption peak area of the elution curve was collected, concentrated, and freeze-dried to obtain the total flavonoid extract from *Gynura formosana* Kitam.

Through calculation, the extraction rate of the total flavonoid extract from *Gynura formosana* Kitam. is 1.91%.

The total flavonoid extract from *Gynura formosana* Kitam. was analyzed by liquid chromatography to determine the content of rutin therein according to the method as described in section B of example 1. According to the resulted HPLC chromatogram, the amount of rutin in the total flavonoid extract was 85% in this example.

Experiment Example 1

Study on treatment of NAFLD rats by the total flavonoid extract from *Gynura formosana* Kitam.

1. Experimental Objectives

This example was carried out to study the treatment effect of the total flavonoid extract from *Gynura formosana* Kitam. on high-fat feed-induced non-alcoholic fatty liver disease (NAFLD) model rats.

2. Materials and Methods 2.1 Experimental Animals 62 healthy male Spague-Dawlay (SD) Rats of SPF grade, each weighed 210±10 g, were provided by Shanghai Sippr BK laboratory animal Co. Ltd. (Certification No: 2007000531494; animal license No.: SCXK (Hu) 2007-0005).

2.2 Test Drugs and Experimental Reagents

The total flavonoid extract from *Gynura formosana* Kitam. prepared in Example 1 was diluted with distilled water to form test drugs of different concentrations: a low dose of 6 mg/10 mL, a medium dose of 12 mg/10 mL, and a high dose of 24 mg/10 mL.

Kits for total triglyceride (TG), total cholesterol (TC), alanine aminotransferase (ALT), aspartic acid transferase (AST), high-density lipoprotein (HDL-C), and low-density lipoprotein (LDL-C) were purchased from NanJing JianCheng Bioengineering Institute. High-fat feed (comprising lard 10%, cholesterol 2%, pig bile salt 0.7%, base feed, 87.3%) was provided by Fuzhou Minhou Zhuqi Animal Service Center. Common feed was provided by Experimental Animal Center of Fujian University of Traditional Chinese Medicine.

2.3 Experimental Instruments

The following instruments were used: Electronic Balance (Ohaus International Trading (Shanghai) Co., Ltd.), BX51T-PHD-J11 Microscope (Olympus, Japan), Low Speed Centrifuge (Thermo, US), Biological Tissue Paraffin Embedding Machine (Yaguang Medical Electronic Technology Co., Ltd, Xiaogan, Hubei), Biological Tissue Automatic Dehydrator (Yaguang Medical Electronic Technology Co., Ltd), Full-Automatic Paraffin Slicing Machine (Leica, Germany), BS-120 Full-Automatic Biochemical Analyzer (Mindray Biomedical Electronics Co. Ltd., Shenzhen).

3. Experimental Methods 3.1 Animal Grouping and Model Establishment

After one week adaptive feeding, 62 male SD rats of SPF-grade were randomly divided into two groups by body weight: a control group (16 rats) and high-fat feed group (46 rats), respectively. Rats in the control group were fed with the base feed, and rats in the high-fat feed group were fed with the high-fat feed. The rats were given free access to water and feed, and exposed to a 12-hour light/dark cycle. The rats were weighed once every week.

After six weeks, 6 rats were randomly selected and sacrificed in each of the control group and the high-fat diet group, and liver tissue was taken to prepare pathological slices. Pathological observation of the slices showed that hepatocyte steatosis was serious in liver of rats in the model group, and hepatocyte steatosis exceeded more than ⅔ per unit area. Serious diffuse large-bubble hepatocyte steatosis, hepatic cell point-like necrosis and moderate fibrosis hyperplasia were observed in the liver tissues, indicating that the non-alcoholic fatty liver disease model was successfully established.

After the model is successfully established, the remaining 40 rats in the high-fat feed group were randomly divided into a model group, a low dose group of the total flavonoid extract, a medium dose group of the total flavonoid extract and a high dose group of the total flavonoid extract, with 10 rats in each group. Starting from the 7th week, rats in the control group and the model group were administered via lavage with saline, and rats in other groups were administered with different doses of the total flavonoid extract, wherein rats in the low dose group was administered with the total flavonoid extract at a dose of 6 mg/10 ml, rats in the medium dose group was administered with the total flavonoid extract at a dose of 12 mg/10 mL, and rats in the high dose group was administered with the total flavonoid extract at a dose of 24 mg/10 mL. At the end of the 10th week, the rats fasted for 12 hours overnight, and next day were anesthetized intraperitoneally with pentobarbital sodium at a dose of 40 mg/kg. Blood was collected from abdominal aortic and centrifuged at 3000 r/min for 15 min to obtain a serum which is then stored in a refrigerator at −80° C. for use in subsequent detection.

3.2 Experimental Data Observation and Detection

During the experiment, the activity, hair gloss, appetite, death and the like of the rats were recorded. Weights of the rats were recorded weekly. Liver and visceral fat pad were collected and weighed. Photos were taken to observe the general morphology of the liver of rats in each group. Then, a portion of the right lobe of liver was fixed with 4% paraformaldehyde solution and routinely embedded in paraffin for pathological slicing. The obtained slices were routinely stained with HE, and observed with an optical microscope. Tissue hepatocyte steatosis, inflammation and necrosis degree were evaluated by referring to the NAFLD diagnosis standard established by the fatty liver and alcoholic liver diseases unit of the Chinese Society of Hepatology. A full-automatic biochemical analyzer was used to determine contents of alanine aminotransferase (ALT), aspartate aminotransferase (ASL), cholesterol (TC), triglyceride (TG), high density lipoprotein (HDL-C), and low density lipoprotein (LDL-C) in serum.

4. Experimental Data Processing

All experimental data were analyzed using software SPSS 18.0. The results were presented in the form of mean value±standard deviation ($\bar{x}$±s). Comparison between data in a plurality of groups was carried out using single-factor variance analysis, and comparison between data of two groups was carried out using a T-test. Count data was analyzed using rank test. P<0.05 was considered statistically significant.

5. Experimental Results 5.1 Effect of the Total Flavonoid Extract From *Gynura formosana* Kitam. on Liver General Morphology of NAFLD Rats Rats in the control group manifested bright red livers with normal size, regular shape, soft texture and smooth surface. Rats in the model group showed obviously swelled livers with a cream-yellow color and an obtuse and thick edge. Diffuse fine particles-like ridges were observed on the liver surface. The slice of the liver was greasy and the texture is relatively brittle. Local yellow white denaturing lesions were observed. Rats in each dose group of the total flavonoid extract manifested slightly swelled livers compared with the normal group. The color is slightly reddish than that of the model group, and is close to the normal color. The slice of the liver was not obviously greasy.

Figure 5:
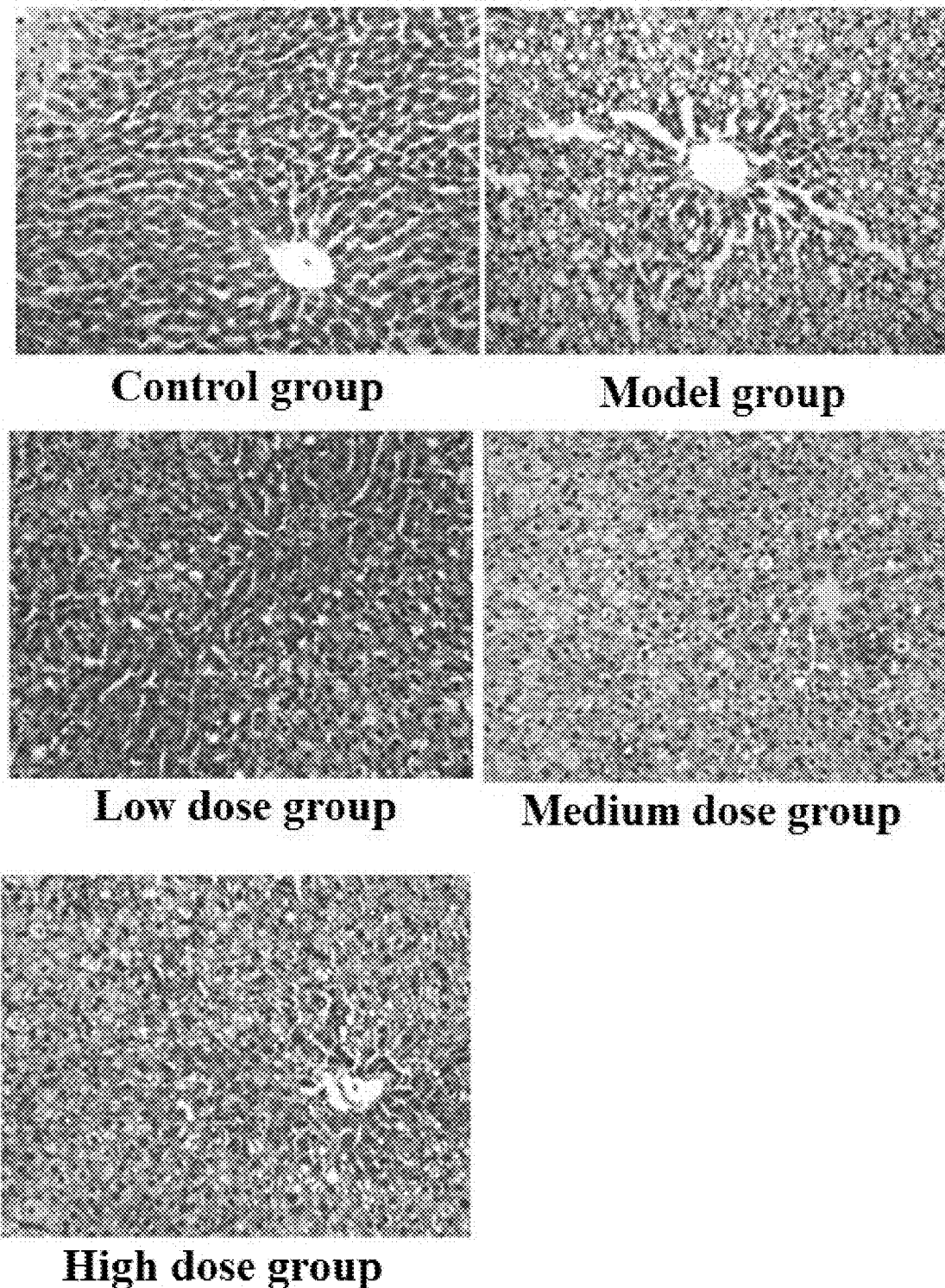
FIG. 5 shows the effect on the liver histopathology of NAFLD rats by the total flavonoid extract from *Gynura formosana* Kitam. prepared in Example 1 of the present invention (40×, HE staining).

5.2 Effect of the Total Flavonoid Extract From *Gynura formosana* Kitam. on Liver Histopathology of NAFLD Rats Effect of the total flavonoid extract from *Gynura formosana* Kitam. on liver histopathology of NAFLD rats is shown in FIG. 5.

By referring to FIG. 5, rats in the control group shows intact structure of hepatic lobule, with clear cellular outline. The central vein is large with thin walls. The hepatic cords are radially arranged. No hepatocyte steatosis and inflammatory cell infiltration were observed. In rats of the model group, diffuse large fat vacuoles were widely observed in cytoplasm of the liver tissue, and the liver cells were swelled. The hepatic cords became disordered and the liver sinuses were narrowed. Cell nucleus was squeezed towards one side. The most obvious lesions were observed around the central vein, including inflammatory cell infiltration which was also involved in hepatic lobule. Main lesions were large fat vacuoles. For rats in each dose group of the total flavonoid extract, the amount and degree of hepatocyte steatosis were obviously reduced compared with the model group, and only small fat vacuoles were observed under the high power microscope.

5.3 Effect of the Total Flavonoid Extract From *Gynura formosana* Kitam. on Liver Weight and Visceral Fat Pad of NAFLD Rats The effect of the total flavonoid extract from *Gynura formosana* Kitam. on liver weight and visceral fat pad of NAFLD rats is shown in Table 1.

TABLE 1

Effect of the total flavonoid extract from *Gynura formosana* Kitam. on liver weight and visceral fat pad of NAFLD rats (n = 10, $\bar{x}$ ± s)

| Group | Dose (mg/10 mL) | Liver weight (g) | Visceral fat pad (g) |
|---|---|---|---|
| Control group | — | 12.88 ± 2.25 | 16.37 ± 4.69 |
| Model group | — | 23.90 ± 3.52## | 19.84 ± 5.94# |
| Low dose group | 6 | 17.70 ± 2.58* | 13.27 ± 3.71* |
| Medium dose group | 12 | 17.00 ± 2.25* | 13.64 ± 2.98* |
| High dose group | 24 | 14.18 ± 1.38* | 13.66 ± 3.48* |

Note:
Compared with the control group,
$p < 0.05$,
$p < 0.01$, and compared with the model group
*$p < 0.05$.

Table 1 shows that, rats in the model group exhibited significantly increased liver weight compared to the control group, and the difference is statistically significant (P<0.01). The difference between each dose group of the total flavonoid extract and the model group is statistically significant (P<0.05). The weight of visceral fat pad (perinephric and epididymal fat) of rats in the model group was significantly increased compared to the control group. Rats in each dose group exhibited reduced liver weight and reduced weight of visceral fat pad, and the difference is statistically significant (P<0.05). However, the difference in the weight of visceral fat pad among the experimental groups is not statistically significant (P>0.05).

5.4 Effect of the Total Flavonoid Extract From *Gynura formosana* Kitam. on Biochemical Indexes in Serum of NAFLD Rats The effect of the total flavonoid extract from *Gynura formosana* Kitam. on biochemical indexes in serum of NAFLD rats is shown in Tables 2 to 4.

TABLE 2

Effect of the total flavonoid extract from *Gynura formosana* Kitam. on TG and TC contents in serum of NAFLD rats (n = 10, $\bar{x} \pm s$)

| Group | Dose (mg/10 mL) | TG (mmol/L) | TC (mmol/L) |
|---|---|---|---|
| Control group | — | 0.54 ± 0.08 | 1.79 ± 0.11 |
| Model group | — | 0.85 ± 0.15# | 2.11 ± 0.22# |
| Low dose group | 6 | 0.62 ± 0.22* | 1.90 ± 0.08* |
| Medium dose group | 12 | 0.51 ± 0.13* | 1.84 ± 0.21* |
| High dose group | 24 | 0.54 ± 0.10* | 1.62 ± 0.25* |

Note:
Compared with the control group,
P < 0.01, and compared with the model group
*P < 0.05.

TABLE 3

Effect of the total flavonoid extract from *Gynura formosana* Kitam. on ALT and AST contents in serum of NAFLD rats (n = 10, $\bar{x} \pm s$)

| Group | Dose (mg/10 mL) | ALT (U/L) | AST (U/L) |
|---|---|---|---|
| Control group | — | 30.69 ± 4.33 | 176.58 ± 38.25 |
| Model group | — | 62.00 ± 13.15# | 268.55 ± 44.71# |
| Low dose group | 6 | 31.11 ± 8.07* | 203.00 ± 35.77* |
| Medium dose group | 12 | 27.43 ± 13.93* | 185.88 ± 42.86* |
| High dose group | 24 | 36.00 ± 7.23* | 180.83 ± 18.06* |

Note:
Compared with the control group,
P < 0.05, and compared with the model group
*P < 0.05.

TABLE 4

Effect of the total flavonoid extract from *Gynura formosana* Kitam. on HDL-C and LDL-C contents of NAFLD rats (n = 10, $\bar{x} \pm s$)

| Group | Dose (mg/10 mL) | HDL-C (mmol/L) | LDL-C (mmol/L) |
|---|---|---|---|
| Control group | — | 0.79 ± 0.09 | 0.95 ± 0.13 |
| Model group | — | 0.52 ± 0.06# | 1.78 ± 0.14# |
| Low dose group | 4.375 | 0.49 ± 0.05 | 1.83 ± 0.10 |
| Medium dose group | 8.75 | 0.46 ± 0.07 | 1.27 ± 0.27* |
| High dose group | 17.5 | 0.55 ± 0.07 | 1.53 ± 0.22* |

Note:
Compared with the control group,
P < 0.05, and compared with the model group
*P < 0.05.

Tables 2 and 3 show that, rats in the model group exhibited a significant increase in TG, TC, ALT and AST contents in serum compared to the control group, and the difference is statistically significant (P<0.05). Rats in each dose group of the total flavonoid extract exhibited a significant decrease in TG, TC, ALT and AST contents in serum compared to the model group, and the difference is statistically significant (P<0.05).

Table 4 shows that, rats in the model group exhibited a significantly increased LDL-C content and a significantly decreased HDL-C content, both differences of which are statistically significant (P<0.05). Rats in each dose group of the total flavonoid extract did not show statistically significant difference in HDL-C content compared to the model group. Rats in medium and high dose groups of the total flavonoid extract showed significantly decreased LDL-C content compared to the model group (P<0.05).

6. Experimental Conclusions

The total flavonoid extract from *Gynura formosana* Kitam. has a good treatment effect on non-alcoholic fatty liver disease, and can obviously improve the blood lipid disorder and hepatocyte steatosis of non-alcoholic fatty liver disease rats.

It is to be understood that the above-described examples are merely illustrative of the embodiments and are not intended to limit the embodiments. It will be apparent to one of ordinary skill in the art that other different forms of changes or variations can be made on the basis of the above description. It is to be understood that various changes or modifications may be made herein without departing from the scope of the invention as defined by the appended claims.

The invention claimed is:

1. A method for treating non-alcoholic fatty liver disease in a human in need thereof comprising administering an extract from *Gynura formosana* Kitam. to the human to effectively treat the non-alcoholic fatty liver disease, wherein the extract comprises 80% wt.-85% wt. of rutin, and is made by the method comprising the steps of:
   (1) extracting *Gynura formosana* Kitam., with an extraction solvent to obtain an extraction solution, and adjusting the extraction solution to a pH of 4-8 to obtain a reaction solution;
   (2) adding an enzyme complex comprising papain, cellulose and pectinase into the reaction solution to carry out enzymolysis through a forced circular reaction at a temperature of 30° C. to 50° C. for 1 hour to 4 hours, then carrying out suction filtration, and collecting a filtrate;
   (3) extracting the filtrate with a macroporous resin A to obtain an extracted solution, and concentrating the extracted solution to obtain a concentrated solution; wherein the macroporous resin A is selected from the group consisting of AB-8, DM-130, HZ841, ZH-00, ZH-01, ZH-02, ZH-03, CAD-40, CAD-45, BS-30 and mixtures thereof; and
   (4) centrifuging the concentrated solution, collecting a supernatant and carrying out elution by using a macroporous resin B, measuring absorbance at a wavelength of 510 nm, collecting the resulting eluate, concentrating and drying the eluate to obtain an extract from *Gynura formosana* Kitam; wherein the macroporous resin B is selected from the group consisting of D-101, D-140, D-141, XAD-3, XAD-4, HP-20, HP-21, LD-605, LSA-10 and mixtures thereof.

2. The method of claim 1, wherein the extract from *Gynura formosana* Kitam. as an active ingredient is mixed with a conventional auxiliary material and prepared according to a conventional process into a pharmaceutical preparation with clinically acceptable forms selected from the group consisting of tablets, capsules, powders, mixtures, pills, granules, syrups, plasters, suppositories, aerosols, ointments and injections.

3. The method of claim 1, wherein a weight ratio of the enzyme complex to the *Gynura formosana* Kitam. is 1:5 to 1:3.

4. The method of claim 1, wherein a weight ratio of papain to cellulase to pectinase in the enzyme complex is (0.5-1.5):(2-5):(1-3).

5. The method of claim 4, wherein the weight ratio of papain to cellulase to pectinase in the enzyme complex is 1:3:2.

6. The method of claim 1, wherein in the extraction in step 1, the extraction solvent is water, and a weight ratio of *Gynura formosana* Kitam. to water is 1:(20-60).

7. The method of claim 1, wherein in step 4, an ethanol aqueous solution with a volume concentration of 70-80% is adopted as an elution solvent, and the elution is performed at a rate of 3-15 m/h; and the concentrated solution comprises a total flavonoid from *Gynura formosana* Kitam. at a concentration of 0.5 mg/mL.

8. The method of claim 3, wherein a weight ratio of papain to cellulase to pectinase in the enzyme complex is (0.5-1.5):(2-5):(1-3).

9. The method of claim 8, wherein the weight ratio of papain to cellulase to pectinase in the enzyme complex is 1:3:2.

10. The method of claim 3, wherein in step 1, the extraction solvent is water, and a weight ratio of *Gynura formosana* Kitam. to water is 1:(20-60).

11. The method of claim 4, wherein in step 3, the extraction solvent is water, and a weight ratio of *Gynura formosana* Kitam. to water is 1:(20-60).

12. The method of claim 3, wherein: in step 4, an ethanol aqueous solution with a volume concentration of 70-80% is adopted as an elution solvent, and the elution is performed at a rate of 3-15 m/h; and the concentrated solution comprises total flavonoid from *Gynura formosana* Kitam. at a concentration of 0.5 mg/mL.

13. The method of claim 4, wherein: in step 4, an ethanol aqueous solution with a volume concentration of 70-80% is adopted as an elution solvent, and the elution is performed at a rate of 3-15 m/h; and the concentrated solution comprises total flavonoid from *Gynura formosana* Kitam. at a concentration of 0.5 mg/mL.

* * * * *